United States Patent [19]

Duchane

[11] 3,932,322

[45] Jan. 13, 1976

[54] WATER ABSORBING STARCH-ACRYLONITRILE GRAFT COPOLYMERS FUMED SILICA OR ALUMINA MODIFIED TO IMPROVE RATE OF ABSORPTION FOR PHYSIOLOGICAL FLUIDS

[75] Inventor: David V. Duchane, Ann Arbor, Mich.

[73] Assignee: Kimberly-Clark Corporation, Neenah, Wis.

[22] Filed: Mar. 7, 1975

[21] Appl. No.: 556,267

[52] U.S. Cl.......... 260/17.4 GC; 128/270; 128/284; 128/285; 128/290 R; 128/290 P
[51] Int. Cl.². . . . . . . . . . . . . . . . . . . . . . . . . . . . . . . . . . . . . . . . . . . C08L 3/00
[58] Field of Search...... 260/17.4 ST, 6 C; 128/284, 128/285, 287, 290 P

[56] References Cited
UNITED STATES PATENTS

| | | | |
|---|---|---|---|
| 2,750,944 | 6/1956 | Tollstrup | 128/290 |
| 3,724,465 | 4/1973 | Duchane | 128/285 |
| 3,783,872 | 1/1974 | King | 128/290 |

*Primary Examiner*—Donald E. Czaja
*Assistant Examiner*—Edward Woodberry
*Attorney, Agent, or Firm*—Daniel J. Hanlon, Jr.; William D. Herrick; Raymond J. Miller

[57] ABSTRACT

An improvement in the composition of particulate, water-insoluble alkali metal carboxylate salts of starch-acrylonitrile graft copolymers of the type which are produced by saponifying starch-acrylonitrile graft copolymers with an alkali metal base in an aqueous alcoholic medium and which particulate copolymer in its unimproved form is capable of absorbing in excess of 50 parts of aqueous fluids per part of copolymer when saturated. The improvement comprises the intermixture with the particulate copolymer of fumed silica or fumed alumina particles in an amount sufficient to increase markedly the rate at which the mixture absorbs physiological fluid as compared to the rate of absorption for such fluids exhibited by the copolymer before the fumed material is added. The mixture also minimizes the undesirable dusting tendency which is a characteristic of the particulate copolymer in the absence of the fumed silica or alumina.

4 Claims, No Drawings

WATER ABSORBING STARCH-ACRYLONITRILE GRAFT COPOLYMERS FUMED SILICA OR ALUMINA MODIFIED TO IMPROVE RATE OF ABSORPTION FOR PHYSIOLOGICAL FLUIDS

BACKGROUND OF THE INVENTION

In recent years, manufacturers of absorbent pads including sanitary napkins, tampons, diapers, bed pads and the like have been interested in incorporating in or adding to the absorbent elements of such pads, supplementary materials capable of absorbing and immobilizing relatively large amounts of aqueous fluid per unit of absorbent used. One purpose of such additives, of course, is to make the pad more compact, and thus more comformable and less conspicuous in use, while increasing the effective absorbency characteristics. In addition when such supplements are used, the total amount of absorbent material necessary to meet a given capacity requirement is reduced and important economies in production cost can be realized.

Among the supplementary materials suggested for this purpose are the water-insoluble alkali metal carboxylate salts of starch-acrylonitrile graft copolymers obtained by saponifying starch-acrylonitrile graft copolymers with an alkali metal base in an aqueous alcoholic medium. These graft copolymers are characterized as "being water-insoluble granular solids having the ability to absorb water in amount in excess of 50 parts per part thereof while retaining their granular character." A detailed description of such compositions may be found in U.S. Pat. No. 3,661,815 which issued May 9, 1972 to T. Smith and is assigned to Grain Processing Corporation.

While these graft copolymers were indeed found to have an extra large capacity for aqueous fluids when tested as indicated in the patent, it was also found that when the copolymer particles were incorporated in tampon or sanitary napkin structures and tested with aqueous saline fluids formulated to simulate menstrual fluids, that such fluids did not penetrate quickly and the potentially large capacity of the polymers was not utilized. Limited tests with menstrual fluids confirmed these results. Apparently, when viscous menstrual fluids first strike the polymers, the particles tend to expand and agglomerate excessively to form a temporary physical barrier against continued unimpaired flow of fluid into the interior of the pads. As a result the rated performance of these modified napkins and tampons with respect to absorption of menstrual fluids was no better than standard products which did not contain a high absorbency additive.

A further disadvantage was noted with respect to use of these copolymer salts is that they are supplied in the form of a powder having small particle size which tend to dust excessively while the tampons and napkins are being fabricated.

This invention is directed to the discovery that the above indicated disadvantages can be overcome by adding certain materials to these graft copolymers which increases the rate at which they absorb menstrual fluids, while at the same time minimizing the dusting problem.

SUMMARY OF THE INVENTION

In accordance with this invention the above disadvantages are overcome by starting with a mass of particulate water-insoluble alkali metal carboxylate salts of starch-acrylonitrile graft copolymers of the type which are produced by saponifying a starch-acrylonitrile graft copolymer with an alkali metal base in an aqueous alcoholic medium and which particulate copolymers before being modified as disclosed herein are capable of absorbing in excess of 50 parts by weight of aqueous fluids per part when saturated, and intermixing therewith a minor quantity of a fumed oxide, such as fumed silica or fumed alumina in an amount sufficient to increase the rate at which said mixture absorbs viscous saline fluids such as menstrual fluids, compared to an equal quantity of the original salt particles, without significantly impairing the total absorbent capacity. This intermixing may be readily accomplished by simply adding the fumed oxide to the polymer in the desired amount and mechanically stirring the two ingredients together. The resulting mixture also has a greatly reduced tendency to dust in contrast to the excessive dusting properties of the original material.

More particularly, and as further defined in U.S. Pat. No. 3,661,815, the polyacrylonitrile may be either polyacrylonitrile or polymethylacrylonitrile; the ratio of acrylonitrile to starch may be in the range of 2:1 to 30:1; the saponifying aqueous alcoholic medium may be methanolic or ethanolic; and the alkali metal base may be sodium, lithium, or potassium hydroxide.

DESCRIPTION OF PREFERRED EMBODIMENTS

In accordance with this invention, various percentages of fumed silica and fumed alumina were added and intermixed with a starch graft copolymer sold under the name of Polymer 35A-100 by Grain Processing Corporation. This polymer is understood to be a starch-acrylonitrile graft polymer with an acylonitriles-tarch ratio of 4:1, which was saponified with an aqueous-ethanolic-KOH solution as described in U.S. Pat. No. 3,661,815 and has a carboxyl content of about 14 percent.

The mixtures of copolymer and the specified fumed inorganic oxides were then tested for rate of water absorption, and rate of synthesized menstrual fluid absorption as follows:

One gram of the product being tested was placed in the bottom of a standard 50 ml. graduated cylinder. Fifty grams of fluid were then added slowly to minimize mixing of the polymer and the fluid. After 15 minutes, the free fluid was poured off, and that which had been absorbed and gelled by the polymer remained behind. This was weighed to determine the amount of fluid absorbed and immobilized by one gram of the product. Fluids used in the tests were pure water and a synthetic physiological fluid having the viscosity and other physical characteristics of menstrual fluid. The test fluid had the following composition:

8.0 G. NaCMC
80.0 G. Glycerine
10.0 G. NaCl
4.0 G. NaHCO$_3$
Distilled water to one liter.

This fluid had a viscosity of about 20 centipoises at 25°C and is hereinafter usually identified as syndate. Syndate is commonly used by those skilled in the art for testing absorbency of catamenial devices. The experiment was run for the polymer alone and for the polymer in thorough admixture with small percentages of fumed silica or fumed alumina as indicated below. Results were as follows:

| Absorbent | Grams Fluid Absorbed Per Gram of Absorbent | | % Increase in Absorption Over Polymer Alone | |
|---|---|---|---|---|
| | Pure Water | Syndate | Pure Water | Syndate |
| Polymer 35A-100; | | | | |
| alone | 28.8 | 4.87 | — | — |
| + 1% Fumed Silica | 28.1 | 7.28 | −2.4 | 49.5 |
| + 2% Fumed Silica | 36.2 | 7.66 | 25.7 | 57.3 |
| + 5% Fumed Silica | — | 6.85 | — | 40.7 |
| +10% Fumed Silica | 32.3 | 6.06 | 12.2 | 24.4 |
| + 1% Fumed Alumina | — | 7.06 | — | 45.0 |
| + 2% Fumed Alumina | 28.2 | 8.91 | −2.1 | 83.0 |
| + 5% Fumed Alumina | 28.5 | 7.56 | −1.0 | 55.2 |
| +10% Fumed Alumina | — | −.98 | — | 63.9 |

The data indicates a remarkable increase in the amount of syndate absorbed by polymer in a 15 minute time span when a small amount of a fumed oxide is added to the copolymer as compared to the copolymer without any additive. It is noted that the marked increase in rate of absorption appears to be peculiar to the syndate, or physiological fluid, since the change in rate with respect to pure water is relatively insignificant except in the case where 2 percent fumed silica is added. In view of the fact that the improvement with which this application is concerned is important only with respect to menstrual and other viscous physiological fluids, only limited testing was done with respect to water alone. In any event, the data indicates the optimum rate of improvement occurs when about 2 percent fumed oxide is added.

The polymer 35A-100 as supplied by Grain Processing Corporation is anionic and water-insoluble, and is in the form of a fine dusty powder of less than 100 mesh particle size. It was discovered that the addition of 1–2 percent fumed silica also has the desirable effect of greatly reducing the dustiness of this product. Fumed alumina has the same effect with respect to reducing dustiness, but to a somewhat lesser degree. The reduction in dustiness of the polymer greatly alleviates handling problems when the material is used as herein described. The reason for the increased rate of absorption and less dustiness is not known, but it is theorized that the fumed oxide particles are so small that they coat the polymer particles by electrostatic attraction. This coating apparently segregates the particles, preventing premature agglomeration when wetted, and thus providing an increased rate of absorption.

Fumed silica is silicon dioxide formed by the vapor phase hydrolysis of silicon tetrachloride. It is supplied in commercial form as a low density waterinsoluble powder with extremely small particle size and a large surface area ranging from 50 to 400 square meters per gram. The fumed silica used in the Examples is sold under the trademark CAB-O-SIL (Type M-5) by Cabot Corporation.

Fumed alumina is aluminum oxide formed by the flame hydrolysis of aluminum chloride. It is also supplied in commercial form as a low density water-insoluble powder with extremely small particle size and a large surface area in the neighborhood of about 100 square meters per gram. The fumed alumina used in the Examples is sold under the trademark ALON-G by Cabot Corporation.

The improved copolymer mixture as defined herein is particularly useful when incorporated in catamenial devices such as sanitary napkins and tampons and particularly with tampons in which it may be incorporated up to 25 percent by weight to improve capacity. Limited tests of tampons containing such amounts of the modified polymer vs. unmodified polymer, indicated the former had an increased rate of absorption since the number of early leakers was substantially reduced as compared to tampons containing the unmodified polymer. Early leakage usually indicates rate of absorption is too slow for the amount of fluid discharged and bypass results even though available absorbent capacity is not utilized.

Broadly, the improved copolymer is especially useful in absorbent devices in which rate of absorption is considered as being equally important as total absorbent capacity. In addition to catamenial devices, other absorbent products in which these characteristics are desirable are disposable diapers, incontinent pads and hospital underpads.

What is claimed is:

1. An improvement in the composition of particulate, water-insoluble alkali metal carboxylate salts of starch-acrylonitrile graft copolymers of the type which are produced by saponifying a starch-acrylonitrile graft copolymer with an alkali metal base in an aqueous alcoholic medium and which particulate copolymer in its unimproved form is capable of absorbing in excess of 50 parts by weight of aqueous fluids per part of copolymer, and in which the molar ratio of the acrylonitrile to the starch in the graft copolymers is in the range of 2:1 to 30:1; said improvement comprising modifying said particulate copolymer by mixing therewith a minor quantity of a fumed oxide selected from the group consisting of fumed silica or fumed alumina in an amount sufficient to increase the rate at which said modified copolymer absorbs saline physiological fluids as compared to the rate at which said unimproved copolymer absorbs said fluids without reducing significantly the total absorbent capacity otherwise exhibited by said unimproved copolymer while minimizing the tendency of said copolymer to dust.

2. An improvement in a water-insoluble, particulate form, alkali metal carboxylate salt of a starch-polyacrylonitrile graft copolymer or a starch-polymethacrylonitrile graft copolymer which copolymer in particulate form is capable of absorbing in excess of 50 parts by weight of aqueous fluids per part of copolymer while maintaining insolubility and which copolymer has been produced by saponifying a starch-polyacrylonitrile or starch-polymethacrylonitrile graft copolymer with an aqueous methanolic or ethanolic solution of an alkali base selected from the group consisting of sodium hydroxide, lithium hydroxide or potassium hydroxide, and in which the molar ratio of the acrylonitrile or methacrylonitrile to the starch in the graft copolymer is in the range of 2:1 to 30:1; said improvement comprising modifying said particulate copolymer by combining and mixing therewith a minor quantity of a fumed oxide selected from the group consisting of fumed silica or fumed alumina, said quantity being in an amount sufficient to markedly increase the rate at which said modified copolymer absorbs saline physiological fluids as compared to the rate at which said particulate copolymer in its unimproved state absorbs said fluids while minimizing the tendency of said copolymer to dust and without reducing significantly the total absorbent capacity otherwise exhibited by said unimproved copolymer.

3. The improved copolymer composition of claim 2 wherein said fumed oxide is added in the amount of in the range of about 1 percent to 10 percent by weight.

4. The improved copolymer composition of claim 2 wherein said fumed oxide is added in the amount of about 2 percent by weight.

* * * * *